(12) United States Patent
Winter et al.

(10) Patent No.: US 6,525,045 B2
(45) Date of Patent: Feb. 25, 2003

(54) POSITIVE ALLOSTERIC AMPA RECEPTOR MODULATORS

(75) Inventors: Karin Winter, Gau-Algesheim (DE); Thomas Weiser, Nieder-Olm (DE); Stefan M. Blech, Warthausen (DE); Angelo Ceci, Biberach (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/774,864

(22) Filed: Jan. 31, 2001

(65) Prior Publication Data

US 2002/0013313 A1 Jan. 31, 2002

(30) Foreign Application Priority Data

Feb. 2, 2000 (DE) .......................................... 100 04 572

(51) Int. Cl.[7] ...................... A61K 31/542; C07D 513/04
(52) U.S. Cl. ......................... 514/224.5; 544/33; 544/14
(58) Field of Search ........................ 514/224.5; 544/33, 544/14

(56) References Cited

U.S. PATENT DOCUMENTS

| 4,895,863 A | 1/1990 | Hedgecock et al. | ........ 514/366 |
|---|---|---|---|
| 5,688,803 A | 11/1997 | Buettelmann et al. | ...... 514/267 |
| 5,985,871 A | 11/1999 | Marrs et al. | ............. 514/229.5 |
| 6,096,744 A | 8/2000 | Kornberg et al. | ........... 514/249 |

FOREIGN PATENT DOCUMENTS

| EP | 0 430 114 A | 6/1991 |
|---|---|---|
| WO | WO93 21170 A | 10/1993 |
| WO | WO98 12185 A | 3/1998 |
| WO | WO99 42456 A | 8/1999 |

*Primary Examiner*—John M. Ford
(74) *Attorney, Agent, or Firm*—Robert P. Raymond; Alan R. Stempel; Mary-Ellen M. Devlin

(57) ABSTRACT

The present invention relates to new positive allosteric AMPA receptor modulators of general formula (I)

(I)

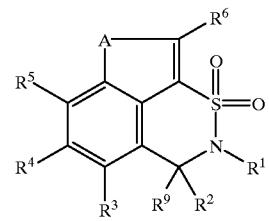

wherein $R^1$, $R^2$ $R^3$, $R^4$, $R^5$ and $R^6$ may have the meanings indicated in the specification and claims, processes for preparing them and their use as pharmaceutical compositions.

9 Claims, No Drawings

POSITIVE ALLOSTERIC AMPA RECEPTOR MODULATORS

FIELD OF THE INVENTION

The present invention relates to novel compounds that are positive allosteric AMPA receptor modulators, processes for preparing them and their use, as pharmaceutical compositions, in the treatment of various disease conditions.

DESCRIPTION OF THE INVENTION

The compounds according to the invention are compounds of general formula (I)

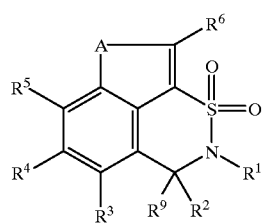

wherein

A denotes a sulphur atom, oxygen atom, NH or N—$C_1$–$C_4$-alkyl, $R^1$ denotes a group selected from among hydrogen, a $C_1$–$C_6$-alkyl group optionally substituted by one or more halogen atoms, —$SO_2H$, —$SO_2$—$C_1$–$C_6$-alkyl, —SO—$C_1$–$C_6$-alkyl, —CO—$C_1$–$C_6$-alkyl, —O, phenyl-$C_1$–$C_4$-alkyl, —$C_1$–$C_4$-alkyl-$NR^7R^8$, —$C_1$–$C_4$-alkyl-O—$C_1$–$C_4$-alkyl and $C_3$–$C_6$-cycloalkyl, $R^2$, $R^9$, which may be identical or different, denote a group selected from among hydrogen, a $C_1$–$C_6$-alkyl group optionally substituted by one or more halogen atoms, halogen, —$NO_2$, —$SO_2H$, —$SO_2$—$C_1$–$C_6$-alkyl, —SO—$C_1$–$C_6$-alkyl, —CO—$C_1$–$C_6$-alkyl, —OH, —O—$C_1$–$C_6$-alkyl, —S—$C_1$–$C_6$-alkyl, —$C_1$–$C_4$-alkyl-$NR^7R^8$ and —$C_1$–$C_4$-alkyl-O—$C_1$–$C_4$-alkyl, $C_3$–$C_6$-cycloalkyl, or $R^1$ and $R^2$ together denote a $C_2$–$C_6$-alkylene bridge, $R^7$, $R^8$, which may be identical or different, denote hydrogen or $C_1$–$C_4$-alkyl, and $R^3$, $R^4$, $R^5$, $R^6$, which may be identical or different, denote a group selected from among hydrogen, a $C_1$–$C_6$-alkyl group optionally substituted by one or more halogen atoms, phenyl-$C_1$–$C_4$-alkyl, halogen, —CN, —$NO_2$, —$SO_2H$, —$SO_3H$, —$SO_2$—$C_1$–$C_6$-alkyl, —SO—$C_1$–$C_6$-alkyl, —$SO_2$—$NR^7R^8$, —COOH, —CO—$C_1$–$C_6$-alkyl, —O—CO—$C_1$–$C_4$-alkyl, —CO—O—$C_1$–$C_4$-alkyl, —CO—$NR^7R^8$, —OH, —O—$C_1$–$C_6$-alkyl, —S—$C_1$–$C_6$-alkyl, —$NR^7R^8$ and an aryl group optionally mono- or polysubstituted by halogen atoms, —$NO_2$, —$SO_2H$ or $C_1$–$C_4$-alkyl, optionally in the form of the various enantiomers and diastereomers thereof, as well as the pharmacologically acceptable salts thereof.

Compounds of general formula (I) are preferred wherein

A denotes a sulphur atom, oxygen atom or N—$C_1$–$C_2$-alkyl, $R^1$ denotes a group selected from among hydrogen, a $C_1$–$C_6$-alkyl group optionally substituted by one or more halogen atoms, —$SO_2H$, —$SO_2$—$C_1$–$C_6$-alkyl, —SO—$C_1$–$C_6$-alkyl, —CO—$C_1$–$C_6$-alkyl, —O, —$C_1$–$C_4$-alkyl-$NR^7R^8$ and —$C_1$–$C_4$-alkyl—O—$C_1$–$C_4$-alkyl, benzyl, $R^2$, $R^9$, which may be identical or different, denote a group selected from among hydrogen, a $C_1$–$C_6$-alkyl group optionally substituted by one or more halogen atoms, halogen, —$NO_2$, —$SO_2H$, —$SO_2$—$C_1$–$C_6$-alkyl, —SO—$C_1$–$C_6$-alkyl, —CO—$C_1$–$C_6$-alkyl, —OH, —O—$C_1$–$C_6$-alkyl, —S—$C_1$–$C_6$-alkyl, —$C_1$–$C_4$-alkyl-$NR^7R^8$ and —$C_1$–$C_4$-alkyl-O—$C_1$–$C_4$-alkyl, or $R^1$ and $R^2$ together denote a $C_3$–$C_6$-alkylene bridge, and $R^3$, $R^4$, $R^5$, $R^6$, which may be identical or different, denote a group selected from among hydrogen, a $C_1$–$C_4$-alkyl group optionally substituted by one or more halogen atoms, phenyl-$C_1$–$C_4$-alkyl, halogen, —CN, —$NO_2$, —$SO_2H$, —$SO_3H$, —$SO_2CH_3$, —$SOCH_3$, —CO—$C_1$–$C_4$-alkyl, —OH, —O—$C_1$–$C_4$-alkyl and —S—$C_1$–$C_4$-alkyl, optionally in the form of the various enantiomers and diastereomers thereof, as well as the pharmacologically acceptable salts thereof.

Compounds of general formula (I) are particularly preferred wherein

A denotes a sulphur atom or N—$C_1$–$C_2$-alkyl, $R^1$, $R^2$, $R^9$, which may be identical or different, denote hydrogen, $C_1$–$C_4$-alkyl, benzyl or $R^1$ and $R^2$ together denote a $C_3$–$C_4$-alkylene bridge, and $R^3$, $R^4$, $R^5$, R6 , which may be identical or different, denote a group selected from among hydrogen, $C_1$–$C_4$-alkyl, $CF_3$, $NO_2$, benzyl, —$SO_2$—$C_1$–$C_4$-alkyl, —$SO_3H$ and halogen, preferably fluorine, chlorine, bromine, most preferably fluorine or chlorine, optionally in the form of the various enantiomers and diastereomers thereof, as well as the pharmacologically acceptable salts thereof.

Also particularly preferred are compounds of general formula (I) wherein

A denotes a sulphur atom or N—$CH_3$, $R^1$, $R^2$, $R^9$ which may be identical or different, denote hydrogen, $C_1$–$C_4$-alkyl or $R^1$ and $R^2$ together denote a $C_3$–$C_4$-alkylene bridge, $R^3$, $R^5$, $R^6$, which may be identical or different, denote a group selected from among hydrogen, $C_1$–$C_4$-alkyl and halogen, preferably fluorine, chlorine, bromine, most preferably fluorine or chlorine, and $R^4$ denotes hydrogen, halogen or $C_1$–$C_4$-alkyl, optionally in the form of the various enantiomers and diastereomers thereof, as well as the pharmacologically acceptable salts thereof.

Of particular importance according to the invention are the compounds of general formula (I) wherein $R^1$ denotes methyl, ethyl, i-propyl, n-butyl or benzyl, optionally in the form of the various enantiomers and diastereomers thereof, as well as the pharmacologically acceptable salts thereof.

Particularly preferred are compounds of general formula (I), wherein

A denotes a sulphur atom, $R^1$ denotes methyl, $R^2$, $R^9$ denote hydrogen, $R^3$ denotes a group selected from among hydrogen, methyl, CN and halogen, preferably fluorine, chlorine, bromine, most preferably fluorine or chlorine, R[5] denotes a group selected from among hydrogen, methyl and halogen, preferably fluorine, chlorine, bromine, most preferably fluorine or chlorine, R[4] denotes hydrogen, and R[6] denotes hydrogen or methyl, preferably hydrogen, optionally in the form of the pharmacologically acceptable salts thereof.

Most particularly preferred are compounds of general formula (I), wherein

A denotes a sulphur atom,

R[1] denotes methyl,

R[3] denotes hydrogen, fluorine or chlorine, and

R[2], R[4], R5, R6, R9 denote hydrogen, optionally in the form of the pharmacologically acceptable salts thereof.

The alkyl groups used, unless otherwise stated, are branched and unbranched alkyl groups having 1 to 6 carbon atoms, preferably I to 4 carbon atoms. Examples include: methyl, ethyl, propyl, butyl, pentyl and hexyl. The groups methyl, ethyl, propyl or butyl may optionally also be referred to by the abbreviations Me, Et, Prop or Bu. Unless otherwise stated, the definitions propyl, butyl, pentyl and hexyl also include all possible isomeric forms of the groups in question. Thus, for example, propyl includes n-propyl and iso-propyl, butyl includes iso-butyl, sec. butyl and tert.-butyl, etc.

In the abovementioned alkyl groups, one or more hydrogen atoms may optionally be substituted by the halogen atoms fluorine, chlorine, bromine or iodine. The substituents fluorine and chlorine are preferred. The substituent fluorine is particularly preferred. If desired, all the hydrogen atoms of the alkyl group may be replaced.

The alkyl group mentioned in the group phenyl-$C_1$–$C_4$-alkyl may be in branched or unbranched form. Unless otherwise stated benzyl and phenylethyl are preferred phenyl-$C_1$–$C_4$-alkyl groups. Benzyl is particularly preferred.

The $C_2$–$C_6$-alkylene bridge may, unless otherwise stated, be branched and unbranched alkylene groups having 2 to 6 carbon atoms, for example ethylene, propylene, methylethylene, dimethylmethylene, n-butylene, 1-methylpropylene, 2-methylpropylene, 1.1-dimethylethylene, 1 .2-dimethylethylene etc. n-Propylene and n-butylene bridges are particularly preferred.

The aryl group is an aromatic ring system having 6–10 carbon atoms, preferably phenyl. In the abovementioned aryl groups, one or more hydrogen atoms may optionally be substituted by halogen atoms, —$NO_2$, —$SO_2H$ or —$C_1$–$C_4$-alkyl, preferably fluorine, chlorine, —$NO_2$, ethyl or methyl, most preferably fluorine or methyl.

The term $C_3$–$C_6$-cycloalkyl denotes saturated cyclic hydrocarbon groups having 3–6 carbon atoms, for example cyclopropyl, cyclobutyl, cyclopentyl or cyclohexyl.

The term halogen, unless otherwise stated, refers to fluorine, chlorine, bromine and iodine, preferably fluorine, chlorine and bromine, most preferably fluorine and chlorine, most preferably fluorine.

As already mentioned, the compounds of formula (I) or the various enantiomers and diastereomers thereof may be converted into the salts thereof, particularly for pharmaceutical use, into the physiologically and pharmacologically acceptable salts thereof. These salts may on the one hand take the form of physiologically and pharmacologically acceptable acid addition salts of the compounds of formula (I) with inorganic or organic acids. On the other hand, the compound of formula (I) where R[1] is hydrogen may be converted by reaction with inorganic bases into physiologically and pharmacologically acceptable salts with alkali or alkaline earth metal cations as counter-ion. The acid addition salts may be prepared, for example, using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above acids. For preparing the alkali and alkaline earth metal salts of the compound of formula (I) wherein R[1] denotes hydrogen, it is preferable to use the alkali and alkaline earth metal hydroxides and hydrides, the hydroxides and hydrides of the alkali metals, especially sodium and potassium, being preferred, while sodium and potassium hydroxide are particularly preferred.

The compounds according to the invention may be prepared in a manner known per se. The following general methods of synthesis shown in Diagrams 1 and 2 below are meant to illustrate the invention without restricting it to their content.

Method 1

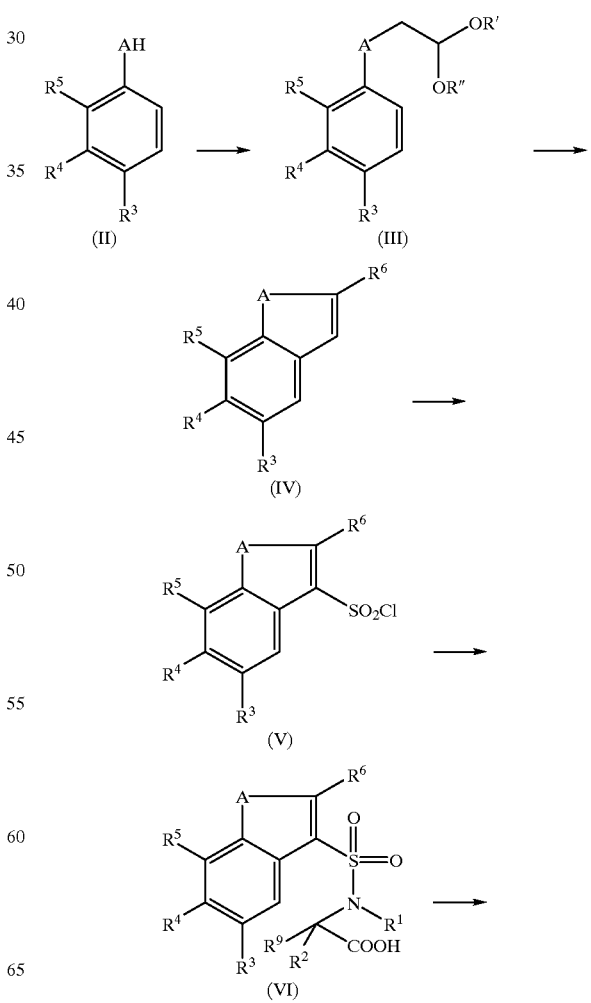

Diagram 1

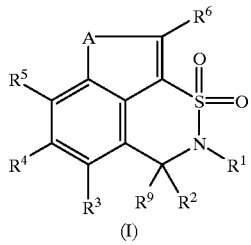

(I)

Starting from a compound of formula (IV) a compound of formula (V) is prepared by sulphonation and subsequent chlorination. The compound of formula (VI) obtained after condensation with aminoacetic acid derivatives is cyclised by the addition of polyphosphoric acid to the target compound (I). Commercially unobtainable compounds of formula (IV) are prepared beforehand by converting the compounds of formula (II) into the compounds of formula (III), wherein $R^\backslash$, $R^{\backslash\backslash}$ which may be identical or different denote C1–C6-alkyl or together denote a 1,2-ethylene or 1,3-propylene group, and subsequently cyclising them under the effect of strong acids.

The general preparation of the compounds according to the invention as shown in Diagram 1 is hereinafter described in more detail with reference to the benzothiophene derivatives (A=S). The process can be carried out analogously with the corresponding indole or benzofuran derivatives:

Synthesis of the diethoxy-ethyl-thiophenols (III):

10 mmol of the thiophenol (II) are dissolved in 2–100 ml, preferably 3–20 ml, most preferably 4 ml of an alcohol, particularly methanol, and combined with 10–50 mmol, preferably 11–30 mmol, most preferably 12 mmol of an alkoxide solution, particularly a sodium ethoxide solution. After 20–120 min, preferably 30 min, 10–50 mmol, preferably 11–30 mmol, most preferably 12 mmol of bromoacetaldehyde dialkylacetal are added and the solution is heated for 2–16 h, preferably 5 h, to 20–100° C., preferably 50–70° C. After evaporation of the solution the residue is divided between an organic solvent and water, particularly taken up with 30 ml of ether and 30 ml of water. The phases are separated and the aqueous phase is then extracted with ether. The combined organic extracts are dried over sodium sulphate and evaporated down in vacuo. The crude product is used in the next reaction without further purification.

Instead of the solvent methanol it is also possible to use ethanol, tetrahydrofuran, toluene, benzene, dimethylformamide, trichloromethane, dichloromethane, acetone or ethyl acetate, instead of the sodium methoxide solution it is possible to use potassium hydroxide, potassium-tert. butoxide, lithium hydroxide, triethylamine, DBU (1,8-diazabicyclo[5.4.0]undec-7-ene), sodium hydride or potassium carbonate as the base.

Synthesis of the benzothiophenes (IV):

10–100 ml, preferably 30 ml, of polyphosphoric acid and 10–250 ml, preferably 40 ml, of chlorobenzene are taken at 140° C. and 10 mmol of the dialkoxy-ethyl-thiophenol (III) are added. After 2–16 h, preferably 5 h, stirring at 90–160° C., preferably 140° C., the phases are separated and the inorganic phase is extracted with ether. The combined organic extracts are dried over $Na_2SO_4$ and evaporated down in vacuo. The residue is purified by distillation.

Instead of the polyphosphoric acid it is possible to use a mixture of phosphorus pentoxide/phosphoric acid and zinc chloride, while toluene or xylene may be used instead of chlorobenzene.

Sulphonation of the benzothiophenes (IV):

10 mmol of the benzothiophene derivative (IV) are dissolved in 2–100 ml, preferably 3–80 ml, most preferably 4 ml, of acetic anhydride and 10 to 100 mmol, preferably 11–80 mmol, most preferably 11 mmol, of conc. sulphuric acid are added dropwise at 0–50° C., preferably 5–20° C. After 2–16 h, preferably 5 h, stirring at 20–100° C., preferably 25 C°, the mixture is poured onto a saturated NaCl solution. The crystals formed are suction filtered and dried.

Instead of acetic anhydride it is possible to use methylene chloride, diisopropylether, ethyl acetate, trichloromethane, toluene, benzene or 1,4-dioxane, while oleum, sulphur trioxide, chlorosulphates or combinations thereof may be used instead of conc. sulphuric acid.

Synthesis of benzothiophene-3-sulphonic acid chlorides (V):

10 mmol of benzothiophene-3-sulphonic acids are combined successively with 10 to 500 mmol, preferably 90 mmol, of phosphorus oxytrichloride and 8–50 mmol, preferably 10 mmol of phosphorus pentachloride and heated for 2–16 h, preferably 5 h, at 20–100° C., preferably by refluxing. The reaction mixture is then evaporated down in vacuo and ice water is added. After extraction with ether the combined organic extracts are dried with disodium sulphate and the solvent is eliminated in vacuo. The crude product obtained is used in the following steps without purification.

Instead of the mixture of phosphorus oxytrichloride/phosphorus pentachloride, it is also possible to use thionyl chloride, phosphorus pentachloride, a mixture of phosphoric acid/chlorine or phosgene. The reaction may alternatively be carried out in the diluents ethyl acetate, water, acetonitrile, N,N-dimethylacetamide, sulpholane, DMF, hexane or dichloroethane.

Synthesis of the benzothiophene-3-sulphonyl-amino-acetic acids:

10 mmol of the chlorosulphonyl-benzothiophenes, 10–100 mmol, preferably 11–30 mmol, most preferably 12 mmol, of aminoacetic acid and 10–100 mmol, preferably 11–30 mmol, most preferably 12 mmol, of sodium hydroxide are dissolved in 16 ml of water and 16 ml of toluene. The reaction mixture is stirred for 2–16 h at 0–110° C., preferably at 65° C., then the phases are separated. The aqueous phase is acidified with 2N hydrochloric acid and extracted with ethyl acetate. The combined organic extracts are dried over sodium sulphate and evaporated down in vacuo. The residue is purified by chromatography. Instead of sodium hydroxide it is possible to use triethylamine, potassium carbonate, sodium hydrogen carbonate or sodium hydride, while instead of toluene it is possible to use tetrahydrofuran, diethylether, dichloromethane, trichloromethane, dioxane, acetone, benzene, ethanol, methanol, ethyl acetate or acetonitrile.

Cyclisation of benzothiophene-3-sulphonyl-amino-acetic acids (VI):

10 mmol of the benzothiophene-3-sulphonyl-aminoacetic acids are combined with 10–200 g, preferably 40 g, of polyphosphoric acid and stirred for 2–16 h, preferably 5 h, at 20–110° C., preferably 75–95° C. Then the reaction mixture is poured onto ice water and extracted with ethyl acetate. The combined organic extracts are dried over disodium sulphate and concentrated by evaporation. The residue is purified by chromatography.

Process 2

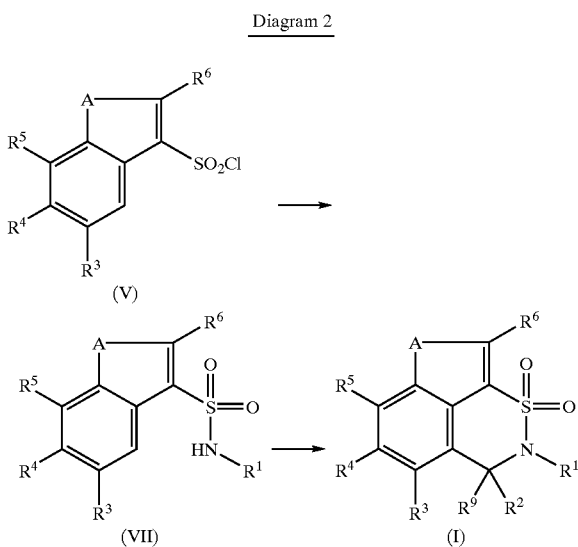

Diagram 2

The compounds of formula (V) prepared as intermediate compounds in process 1 are reacted with primary amines to form the compounds of formula (VII) and then cyclised by the addition of a compound of formula $R^2R^9C\!=\!O$ in the presence of strong acid to form the target compounds (I).

Paraformaldehyde, trioxane or formalin may be used to prepare the compounds of formula (I) wherein $R^1$ and $R^2$ denote hydrogen, while methanesulphonic acid, trifluoroacetic acid, sulphuric acid, phosphoric acid or polyphosphoric acid may be used as strong acids.

The general preparation of the compounds according to the invention as shown in Diagram 2 is described hereinafter with reference to the benzothiophene derivatives (A=S). The process can be carried out analogously with the corresponding indole or benzofuran derivatives.
Synthesis of the benzothiophene-sulphonamides (VII):

10 mmol of the chloro-benzothiophene-sulphonic acids (V) are combined with an alcoholic solution of the primary amine (10–1000 mmol in 5–200 ml, for example 200 mmol in 50 ml ethanol) and then heated for 2–16 h, preferably 5 h at 0–100 C°, preferably by refluxing. The reaction mixture is then evaporated down in vacuo and purified by chromatography.

Instead of the alcoholic solvent it is possible to use toluene, benzene, trichloromethane, dichloromethane, diethylether, tetrahydrofuran, water, acetonitrile, acetic anhydride, acetone, pyridine, dimethylsulphoxide, dimethylformamide, dioxane or hexane.
Cyclisation of the benzothiophene-sulphonamides (VII) into the target compounds (I):

10 mmol of the benzothiophene-sulphonamides are dissolved in 0–100 ml, preferably 20–80 ml, most preferably about 40 ml of methanesulphonic acid and combined with a solution of 3–50 mmol, preferably 4–30, most preferably 5 mmol of trioxane in 0–100 ml, preferably about 12 ml of trifluoroacetic acid. The reaction mixture is stirred for 2–16 h, preferably 5 h, at 20–100 C°, preferably 30–80° C., most preferably 35° C. and then poured onto ice water. After extraction with ether and drying of the combined organic extracts over $Na_2SO_4$ the solution is concentrated by evaporation. The crude product is purified by chromatography.

Instead of trioxane it is possible to use paraformaldehyde or formalin, while instead of trifluoroacetic acid it is possible to use boron trifluoride*diethylether, acetic acid, polyphosphoric acid, phosphoric acid or sulphuric acid. Acetic anhydride or dichloromethane may be used as possible solvents. The new compounds of general formula (I) may be synthesised analogously to the following examples of synthesis. However, these Examples are intended solely as examples of procedure to illustrate the invention, without restricting it to their content.
Synthesis of 4-methyl-4,5-dihydro-1,3-dithia-4-aza-acenaphthylene 3,3-dioxide

EXAMPLE 1

Step 1: sodium-benzothiophene-3-sulphonate:
20 g of benzothiophene are placed in 25 ml of acetic anhydride, cooled to 5° C., and 8.7 ml of conc. sulphuric acid are slowly added thereto. After a reaction time of 2 hours at ambient temperature the solution is poured onto 400 ml of ice water and then washed with 250 ml of diethylether. By the addition of NaCl the product is separated out from the aqueous solution, the white solid precipitated is suction filtered and dried in the drying cupboard at 60° C. Yield: 26 g.
Step 2: 3-Chlorosulphonyl-1-benzothiophene:

180 g of sodium-benzothiophene-3-sulphonate are placed in 650 ml of phosphorus oxychloride and then combined with 156 g of phosphorus pentachloride. The reaction mixture is refluxed for 3.5 hours before the excess phosphorus oxychloride is eliminated by distillation in vacuo. The residue is taken up in 800 ml of chloroform and the precipitate formed is separated off by filtering. The filtrate is concentrated by evaporation and stirred into 800 ml of petroleum ether with heating. The crystalline substance thus precipitated is filtered off, washed with petroleum ether and dried at 35° C.
Yield: 113 g. M.p.: 88–89° C.
Step 3: [(benzothiophene-3-sulphonyl)-methyl-amino]-acetic acid:

6 g of NaOH, 23.27 g of 3-chlorosulphonyl-benzothiophene and 13.36 g of sarcosine are added to a mixture of 200 ml of toluene and 200 ml of water and stirred for 6.5 hours at 60° C. For working up, the aqueous phase is separated off and the organic phase is extracted with 100 ml of 2 N NaOH solution. The combined aqueous phases are acidified with conc. HCl and then extracted twice with 300 ml of ethyl acetate. After washing with saturated aqueous saline solution and drying over magnesium sulphate the organic phase is concentrated by evaporation. The crude product obtained is recrystallised from 100 ml of dichloroethane. Yield: 13.14 g. M.p.: 139–140° C.
Step 4: 4.5-Dihydro-4-methyl-3.3-dioxide-thieno[2,3 4-ij]j [2.3]benzothiazine:

110 g polyphosphoric acid are combined with 10.5 g of [(benzothiophene-3-sulphonyl)-methyl-amino]-acetic acid and stirred for 75 min at 70–75° C., whereupon there is a vigorous development of gas. The reaction mixture is stirred into 1 l of warm water and extracted three times with 250 ml of methylene chloride. The combined organic phases are washed with 300 ml of a 2 N NaOH solution and then dried over magnesium sulphate. The residue remaining after evaporation is purified by chromatography. Yield: 3.8 g. M.p.: 149–150° C.
Synthesis of 4-ethyl-4.5-dihydro-1,3-dithia-4-aza-acenaphthylene 3,3-dioxide

EXAMPLE 2

1.90 g of N-ethyl-benzo[b]thiophene-3-sulphonamide are dissolved in 25 ml methanesulphonic acid at 35° C. and combined with a solution of 0.29 g of trioxane in 8 ml of trifluoroacetic acid. After 2.5 h stirring at ambient temperature the reaction mixture is poured onto 400 ml of ice water. The solid formed is separated off by filtration, washed with 200 ml of water and then dissolved while hot in 400 ml of ethanol/isopropanol (1:1) and separated from solid residues by filtering again. The residue remaining after the concentration of the filtrate is purified by chromatography. Yield: 0.82 g. M.p.: 156° C.

Synthesis of 8-chloro-4-methyl-4,5-dihydro-1,3-dithia-4-aza-acenaphthylene 3,3-dioxide

EXAMPLE 3

0.2 g of 7-chloro-benzo[b]thiophene-3-sulphonic acid-methylamide are dissolved in 3 ml of methanesulphonic acid at 35° C. and combined with a solution of 0.03 g of trioxane in 0.9 ml trifluoroacetic acid. After 2 h stirring at 35° C. the reaction mixture is poured onto 100 ml of ice water and the aqueous phase is extracted with ethyl acetate. The combined organic extracts are dried with $Na_2SO_4$, evaporated down in vacuo and then purified by chromatography. Yield: 0.06 g. M.p.: 146° C.

Synthesis of 6-fluoro-4-methyl-4,5-dihydro-1,3-dithia-4-aza-acenaphthylene 3,3-dioxide

EXAMPLE 4

0.37 g of 5-fluoro-benzo[b]thiophene-3-sulphonic acid-methylamide are dissolved in 5.9 ml of methanesulphonic acid at 35° C. and combined with a solution of 0.06 g of trioxane in 1.8 ml of trifluoroacetic acid. After 2.5 h stirring at 35° C. the reaction mixture is poured onto 100 ml of ice water and the aqueous phase is extracted with ethyl acetate. The combined organic extracts are dried with $Na_2SO_4$, evaporated down in vacuo and then purified by chromatography. Yield: 0.22 g. M.p.: 175° C.

Synthesis of 6-chloro-4-methyl-4,5-dihydro-1.3-dithia-4-aza-acenaphthylene 3.3-dioxide

EXAMPLE 5

0.60 g of 5-chloro-benzo[b]thiophene-3-sulphonic acid-methylamide are dissolved in 8.9 ml of methanesulphonic acid at 35° C. and combined with a solution of 0.09 g trioxane in 2.7 ml trifluoroacetic acid. After 3 h stirring at 35° C. the reaction mixture is poured onto 100 ml of ice water and the aqueous phase is extracted with ethyl acetate. The combined organic extracts are dried with $Na_2SO_4$, evaporated down in vacuo and then purified by chromatography. Yield: 0.30 g. M.p.: 196° C.

Synthesis of 1,4-dimethyl-4,5-dihydro-1H-3-thia-1,4-diaza-acenaphthylene 3.3-dioxide

EXAMPLE 15

4 g of N,N'-dimethylindole-3-sulphonamide are dissolved in 100 ml methanesulphonic acid at 35° C. and combined with 0.54 g of trioxane in 25 ml trifluoroacetic acid. After 1 h stirring at 35° C. the reaction mixture is poured onto ice and the aqueous phase is extracted with ethyl acetate. The combined organic extracts are dried with Na2SO4, evaporated down in vacuo and then purified by chromatography. Yield: 0.07 g. M.p.: 190° C.

4-methyl-3,3-dioxo-4,5-dihydro-3H-1,3-dithia-4-aza-acenaphthylene-6-carbonitrile

EXAMPLE 16

1 g of 6-bromo-4-methyl-4,5-dihydro-1,3-dithia-4-aza-acenaphthylene -3,3-dioxide is added to 0.32 g of copper (I) cyanide and 10 ml of pyridine. The reaction mixture is heated to 190° C. for 7 h, then poured onto 10 ml of ammonia solution and combined with water and ether (30 ml of each). The aqueous phase is extracted with ether. The combined organic phases are washed with 10 ml of dilute hydrochloric acid and then dried over $Na_2SO_4$. After the solution has been evaporated down in vacuo it is purified by chromatography. Yield: 0.06 g. M.p. 238° C.

The following compounds of formula IA wherein Ph denotes phenyl are obtained inter alia analogously to the process described hereinbefore:

TABLE 1

(IA)

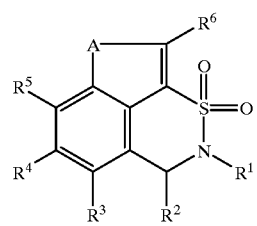

| Ex. | $R^1$ | $R^2$ | $R^3$ | $R^4$ | $R^5$ | $R^6$ | A | M.p. [° C.] |
|---|---|---|---|---|---|---|---|---|
| 1 | $CH_3$ | H | H | H | H | H | S | 149–150 |
| 2 | $C_2H_5$ | H | H | H | H | H | S | 156 |
| 3 | $CH_3$ | H | H | H | Cl | H | S | 146 |
| 4 | $CH_3$ | H | F | H | H | H | S | 175 |
| 5 | $CH_3$ | H | Cl | H | H | H | S | 196 |
| 6 | $CH_3$ | H | H | H | H | $CH_3$ | S | 208 |
| 7 | $CH_3$ | H | $CH_3$ | H | H | H | S | 187 |
| 8 | $CH_2$—Ph | H | H | H | H | H | S | 74 |
| 9 | i-$C_3H_7$ | H | H | H | H | H | S | 117 |

TABLE 1-continued

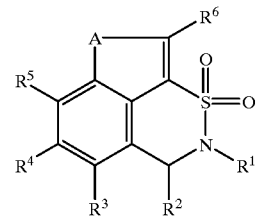

(IA)

| Ex. | R¹ | R² | R³ | R⁴ | R⁵ | R⁶ | A | M.p. [° C.] |
|---|---|---|---|---|---|---|---|---|
| 10 | $CH_3$ | H | H | H | $CH_3$ | H | S | 136 |
| 11 | $CH_3$ | H | Br | H | H | H | S | 203 |
| 12 | $n\text{-}C_4H_9$ | H | H | H | H | H | S | 91 |
| 13 | $CH_3$ | H | Cl | H | Cl | H | S | 164 |
| 14 | $-CH_2-CH_2-CH_2-$ | H | H | H | H | H | S | 149 |
| 15 | $CH_3$ | H | H | H | H | H | $N-CH_3$ | 190 |
| 16 | $CH_3$ | H | CN | H | H | H | S | 238 |
| 17 | $CH_3$ | H | H | H | $i\text{-}C_3H_7$ | H | S | 125 |
| 18 | $CH_3$ | H | H | H | H | H | O | |
| 19 | $C_2H_5$ | H | H | H | H | H | O | |
| 20 | $CH_3$ | H | H | H | Cl | H | O | |
| 21 | $CH_3$ | H | F | H | H | H | O | |
| 22 | $CH_3$ | H | Cl | H | H | H | O | |
| 23 | $CH_3$ | H | H | F | H | H | S | |
| 24 | $CH_3$ | H | H | H | F | H | S | |
| 25 | $CH_3$ | H | $SO_3H$ | H | H | H | S | |
| 26 | $CH_3$ | H | H | $SO_3H$ | H | H | S | |
| 27 | $CH_3$ | H | H | H | $SO_3H$ | H | S | |
| 28 | $CH_3$ | H | $CF_3$ | H | H | H | S | |
| 29 | $CH_3$ | H | H | $CF_3$ | H | H | S | |
| 30 | $CH_3$ | H | H | H | $CF_3$ | H | S | |
| 31 | $CH_3$ | H | F | H | $CF_3$ | H | S | |
| 32 | $CH_3$ | H | $NO_2$ | H | H | H | S | |
| 33 | $CH_3$ | H | H | $NO_2$ | H | H | S | |
| 34 | $CH_3$ | H | H | H | $NO_2$ | H | S | |
| 35 | $CH_3$ | H | F | H | $NO_2$ | H | S | |
| 36 | $CH_3$ | $CH_3$ | H | H | H | $CH_3$ | S | |
| 37 | H | H | H | H | H | H | S | |
| 38 | H | H | F | H | H | H | S | |
| 39 | H | $CH_3$ | H | H | H | $CH_3$ | S | |
| 40 | $C_2H_4-N(CH_3)_2$ | H | H | H | H | H | S | |
| 41 | $CH_3$ | $CF_3$ | H | H | H | H | S | |
| 42 | $CH_3$ | F | H | H | H | H | S | |
| 43 | $CH_3$ | H | H | H | H | $CO_2C_2H_4$ | S | |
| 44 | $CH_3$ | Ph | H | H | H | H | S | |
| 45 | $CH_3$ | H | Ph | H | H | H | S | |
| 46 | $CH_3$ | H | H | H | Ph | H | S | |
| 47 | $CH_3$ | H | OH | H | H | H | S | |
| 48 | $CH_3$ | H | H | H | OH | H | S | |
| 49 | $CH_3$ | H | H | $OCH_3$ | H | H | S | |
| 50 | $CH_3$ | H | $N(CH_3)_2$ | H | H | H | S | |
| 51 | $CH_3$ | H | F | H | $N(CH_3)_2$ | H | S | |
| 52 | $CH_3$ | H | F | F | F | H | S | |

It has been found that the compounds of general formula (I) are characterised by their great wide range of applications in the therapeutic field. Particular mention should be made of those applications in which the positive modulation of AMPA receptors plays a part. The effect of the compounds according to the invention as AMPA receptor modulators was measured electrophysiologically on cells which express functional AMPA receptors. Investigations were carried out to see whether the test substances have a positive allosteric influence on the agonist-induced current.

The test was carried out at concentrations of between 0.3 μmol and 300 μmol.

TABLE 2

Intensification of the agonist-induced current
(+ good, ++ very good activity)

| Example | Effectiveness |
|---|---|
| 1 | ++ |
| 2 | + |
| 3 | + |
| 4 | ++ |
| 5 | + |

The new compounds can also be used to treat illnesses or conditions in which neuronal networks which require AMPA receptors in order to function are damaged or limited in their function.

The compounds of general formula (I) can thus be used in dementias, in neurodegenerative or psychotic illnesses and in neurodegenerative disorders and cerebral ischaemias of various origins, preferably in schizophrenia or learning and memory disorders.

The following are also included: epilepsy, hypoglycaemia, hypoxia, anoxia, cerebral trauma, brain oedema, amyotropic lateral sclerosis, Huntington's Disease, Alzheimer's disease, sexual dysfunction, disorders of sensory/motor function, memory formation, hyperkinetic behavioural changes (particularly in children), hypotension, cardiac infarct, cerebral pressure (increased intracranial pressure), ischaemic and haemorrhagic stroke, global cerebral ischaemia on stoppage of the heart, acute and chronic neuropathic pain, diabetic polyneuropathy, tinnitus, perinatal asphyxia, psychoses, Parkinson's disease and depression, and related anxiety states.

The new compounds may also be given in conjunction with other active substances, such as those used for the same indications, or for example with neuroleptics, nootropics, psychostimulants, etc. They may be administered topically, orally, transdermally, nasally, parenterally or by inhalation. Moreover, the compounds of general formula I or the salts thereof may also be combined with active substances of other kinds.

The compounds of general formula (I) may be given on their own or in conjunction with other active substances according to the invention, and possibly also in conjunction with other pharmacologically active substances. Suitable preparations include for example tablets, capsules, suppositories, solutions,—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof. Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, particularly orally. For oral administration the tablets may of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1–1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The following examples of formulations illustrate the present invention without restricting its scope:

Examples of Pharmaceutical Formulations

| A) Tablets | per Tablet |
|---|---|
| active substance | 100 mg |
| lactose | 140 mg |
| maize starch | 240 mg |
| polyvinylpyrrolidone | 15 mg |
| magnesium stearate | 5 mg |
| | 500 mg |

The finely-ground active substance, lactose and some of the maize starch are mixed together. The mixture is screened, then moistened with a solution of polyvinylpyrrolidone in water, kneaded, wet-granulated and dried. The granules, the remaining maize starch and the magnesium stearate are screened and mixed together. The mixture is compressed to produce tablets of suitable shape and size.

| B) Tablets | per Tablet |
|---|---|
| active substance | 80 mg |
| lactose | 55 mg |
| maize starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance | 50 mg |
| sodium chloride | 50 mg |
| aqua for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

What is claimed is:

1. A compound of the formula (I)

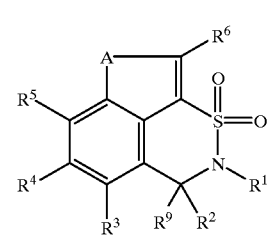

(I)

wherein:

A is a sulphur atom, oxygen atom, >NH or >N—$C_1$–$C_4$-alkyl;

$R^1$ is a group selected from the group consisting of hydrogen, $C_1$–$C_6$-alkyl optionally substituted by one or more halogen atoms, —$SO_2H$, —$SO_2$—$C_1$–$C_6$-alkyl, —SO—$C_1$–$C_6$-alkyl, —CO—$C_1$–$C_6$-alkyl, —$O^-$, $C_1$–$C_4$-alkyl substituted by a phenyl, —$C_1$–$C_4$-alkyl-$NR^7R^8$, —$C_1$–$C_4$-alkyl-O—$C_1$–$C_4$-alkyl and, —$C_3$–$C_6$-cycloalkyl;

$R^2$ and $R^9$ are identical or different and each is a group selected from the group consisting of hydrogen, $C_1$–$C_6$-alkyl optionally substituted by one or more halogen atoms, halogen, —$NO_2$, —$SO_2H$, —$SO_2$—$C_1$–$C_6$-alkyl, —SO—$C_1$–$C_6$-alkyl, —CO—$C_1$–$C_6$-alkyl, —OH, —O—$C_1$–$C_6$-alkyl, —S—$C_1$–$C_6$-alkyl, —$C_1$–$C_4$-alkyl-$NR^7R^8$, —$C_1$–$C_4$-alkyl-O—$C_1$–$C_4$-alkyl and —$C_3$–$C_6$-cycloalkyl; or, $R^1$ and $R^2$ together form a $C_2$–$C_6$-alkylene bridge;

$R^7$ and $R^8$ are identical or different and each is hydrogen or $C_1$–$C_4$-alkyl; and, $R^3$, $R^4$, $R^5$ and $R^6$ are identical or different and each is a group selected from the group consisting of hydrogen, $C_1$–$C_6$-alkyl optionally substituted by one or more halogen atoms, $C_1$–$C_4$-alkyl substituted by a phenyl, halogen, —CN, —$NO_2$, —$SO_2H$, —$SO_3H$, —$SO_2$—$C_1$–$C_6$-alkyl, —SO—$C_1$–$C_6$-alkyl, —$SO_2$—$NR^7R^8$, —COOH, —CO—$C_1$–$C_6$-alkyl, —O—CO—$C_1$–$C_4$-alkyl, —CO—O—$C_1$–$C_4$-alkyl, —CO—$NR^7R^8$, —OH, —O—$C_1$–$C_6$-alkyl, —S—$C_1$–$C_6$-alkyl, —$NR^7R^8$ and aromatic ring systems having 6–10 carbon atoms (wherein one or more hydrogen atoms are optionally substituted by a halogen atom, —$NO_2$, —$SO_2H$ or —$C_1$–$C_4$-alkyl);

or a pharmacologically acceptable salt thereof.

2. A compound of the formula (I) according to claim 1, wherein:

A is a sulphur atom, oxygen atom or >N—$C_1$–$C_2$-alkyl;

$R^1$ is a group selected from the group consisting of hydrogen, $C_1$–$C_6$-alkyl optionally substituted by one or more halogen atoms, —$SO_2H$, —$SO_2$—$C_1$–$C_6$-alkyl, —SO—$C_1$–$C_6$-alkyl, —CO—$C_1$–$C_6$-alkyl, —$O^-$, —$C_1$–$C_4$-alkyl-$NR^7R^8$, —$C_1$–$C_4$-alkyl-O—$C_1$–$C_4$-alkyl and benzyl;

$R^2$ and $R^9$ are identical or different and each is a group selected from the group consisting of hydrogen, $C_1$–$C_6$-alkyl optionally substituted by one or more halogen atoms, halogen, —$NO_2$, —$SO_2H$, —$SO_2$—$C_1$–$C_6$-alkyl, —SO—$C_1$–$C_6$-alkyl, —CO—$C_1$–$C_6$-alkyl, —OH, —O—$C_1$–$C_6$-alkyl, —S—$C_1$–$C_6$-alkyl, —$C_1$–$C_4$-alkyl-$NR^7R^8$ and —$C_1$–$C_4$-alkyl-O—$C_1$–$C_4$-alkyl; or, $R^1$ and $R^2$ together form a $C_3$–$C_6$-alkylene bridge; and, $R^3, R^4, R^5, R^6$ are identical or different and each is a group selected from the group consisting of hydrogen, $C_1$–$C_4$-alkyl optionally substituted by one or more halogen atoms, $C_1$–$C_4$-alkyl substituted by a phenyl, halogen, —CN, —NO$_2$, —SO$_2$H, —SO$_3$H, —SO$_2$CH$_3$, —SOCH$_3$, —CO—$C_1$–$C_4$-alkyl, —OH, —O—$C_1$–$C_4$-alkyl and —S—$C_1$–$C_4$-alkyl;

or a pharmacologically acceptable salt thereof.

3. A compound of general formula (I) according to claim 1, wherein:

A is a sulphur atom or >N—$C_1$–$C_2$-alkyl;

$R^1, R^2, R^9$ are identical or different and each is hydrogen, $C_1$–$C_4$-alkyl or benzyl; or, $R^1$ and $R^2$ together form a $C_3$–$C_4$-alkylene bridge; and $R^3, R^4, R^5, R^6$ are identical or different and each is a group selected from the group consisting of hydrogen, $C_1$–$C_4$-alkyl, CF$_3$, NO$_2$, benzyl, —SO$_2$—$C_1$–$C_4$-alkyl, —SO$_3$H and halogen;

or a pharmacologically acceptable salt thereof.

4. A compound of the formula (I) according to claim 1, wherein:

A is a sulphur atom or >N—CH$_3$;

$R^1, R^2, R^9$ are identical or different and each is hydrogen or $C_1$–$C_4$-alkyl; or, $R^1$ and $R^2$ together form a $C_3$–$C_4$-alkylene bridge;

$R^3, R^5, R^6$ are identical or different and each is a group selected from the group consisting of hydrogen, $C_1$–$C_4$-alkyl and halogen; and, $R^4$ is hydrogen, halogen or $C_1$–$C_4$-alkyl;

or a pharmacologically acceptable salt thereof.

5. A compound of the formula (I) according to claim 4, wherein:

$R^1$ is methyl, ethyl, i-propyl, n-butyl or benzyl;

or a pharmacologically acceptable salt thereof.

6. A compound of the formula (I) according to claim 1, wherein:

A is a sulphur atom;

$R^1$ is methyl;

$R^2$ and $R^9$ are both hydrogen;

$R^3$ is hydrogen, methyl, CN or halogen;

$R^5$ is hydrogen, methyl or halogen;

$R^4$ is hydrogen; and, $R^6$ is hydrogen or methyl;

or a pharmacologically acceptable salt thereof.

7. A compound of the formula (I) according to claim 1, wherein:

A is a sulphur atom;

$R^1$ is methyl;

$R^3$ is hydrogen, fluorine or chlorine; and, $R^2, R^4, R^5, R^6$ and $R^9$ are each hydrogen;

or a pharmacologically acceptable saltsthereof.

8. A method of treating impaired memory which method comprises administering to a host in need of such treatment a therapeutic amount of a compound of the Formula I in accordance with claim 1, 2, 3, 4, 5, 6 or 7.

9. A pharmaceutical composition comprising a compound of the Formula I in accordance with claim 1, 2, 3, 4, 5, 6 or 7 and a pharmaceutically acceptable carrier.

* * * * *